(12) United States Patent
Kumar (10) Patent No.: US 8,569,062 B2
(45) Date of Patent: Oct. 29, 2013

(54) CRYOGELS OF PVA-BORONIC ACID CONTAINING CO-POLYMERS FOR CELL CULTURE

(75) Inventor: Ashok Kumar, Jammu (IN)

(73) Assignee: Indian Institute of Technology Kanpur, Kanpur (IN)

( * ) Notice: Subject to any disclaimer, the term of this patent is extended or adjusted under 35 U.S.C. 154(b) by 0 days.

(21) Appl. No.: 13/880,020

(22) PCT Filed: Aug. 8, 2011

(86) PCT No.: PCT/IB2011/053522
§ 371 (c)(1),
(2), (4) Date: Apr. 17, 2013

(87) PCT Pub. No.: WO2012/176024
PCT Pub. Date: Dec. 27, 2012

(65) Prior Publication Data
US 2013/0217127 A1    Aug. 22, 2013

(30) Foreign Application Priority Data
Jun. 23, 2011 (IN) .......................... 1775/DEL/2011

(51) Int. Cl.
C12N 5/02       (2006.01)
C08G 18/38     (2006.01)

(52) U.S. Cl.
USPC ........... 435/397; 435/179; 435/180; 502/405; 521/62; 521/73; 521/82; 521/85; 521/103; 521/105

(58) Field of Classification Search
USPC ........ 435/397, 179, 180; 521/62, 73, 82, 103, 521/105, 85; 502/405
See application file for complete search history.

(56) References Cited

U.S. PATENT DOCUMENTS

| | | | |
|---|---|---|---|
| 5,981,826 A | 11/1999 | Ku et al. | |
| 6,350,527 B1 | 2/2002 | Hubbell et al. | |
| 2009/0170973 A1* | 7/2009 | Mattiasson et al. | 521/134 |
| 2011/0059176 A1 | 3/2011 | Moro et al. | |

OTHER PUBLICATIONS

Chapekar, M. S. "Tissue engineering: challenges and opportunities," J. Biomed. Mater. Res. (Appl. Biomater.) 53, 617-620 (2000).
Efremenko, E.N. et al., "The Effect of Long-term Preservation of Bacterial Cells Immobilized in Poly(vinyl alcohol) Cryogel on their Viability and Biosynthesis of Target Metabolites," Microbiology, 2007, vol. 76(3), pp. 336-341.
Hisamitsu, I., et al., "Glucose-responsive gel from phenylborate polymer and poly(vinylalcohol): prompt response at physiological pH through the interaction of borate with amino group in the gel," Pharm. Res. 14, 289-293 (1997).
International Search Report and Written Opinion received for PCT/IB2011/053522 mailed Dec. 6, 2011.
Ivanov, A.E. et al., "Boronate-containing polymers form affinity complexes with mucin and enable tight and reversible occlusion of mucosal lumen by poly(vinyl alcohol) gel," Int J Pharm, 2008, vol. 358, pp. 36-43.
Ivanov, A.E. et al., "Synthesis of boronate-containing copolymers of N,N-dimethylacrylamide, their interaction with poly(vinyl alcohol) and rheological behaviour of the gels," Polymer, 2004, vol. 45, pp. 2495-2505.
Jain, E., et al., "Macroporous interpenetrating cryogel network of poly(acrylonitrile) and gelatin for biomedical applications," J Mater Sci: Mater Med (2009) 20, pp. S173-S179.
Kitano, S., et al., "A novel drug delivery system utilising a glucose responsive polymer complex between poly(vinyl alcohol) and poly(N-vinyl-2-pyrrolidone) with a phenylboronic acid moiety," J. Control. Release. 19, 161-70 (1992).
Kitano, S., et al., "Glucose-responsive complex formation between poly(vinyl alcohol) and poly(Nvinyl-2-pyrrolidone) with pendent phenylboronic acid moieties," Makromol. Chem., Rapid. Commun. 12, 227-33 (1991).
Langer, R. et al., "Tissue Engineering," Science. 460, May 14, 1993, pp. 920-926.
Liu, X., C. et al., "New ligands for boronate affinity chromatography," J. Chromatogr A. 687, 61-69 (1999).

(Continued)

Primary Examiner — Susan Hanley
(74) Attorney, Agent, or Firm — Foley & Lardner LLP (57) ABSTRACT

The present invention relates to a cryogel which contains a polyol selected from polyvinyl alcohol or galactomannan and a co-polymer of Formula I:

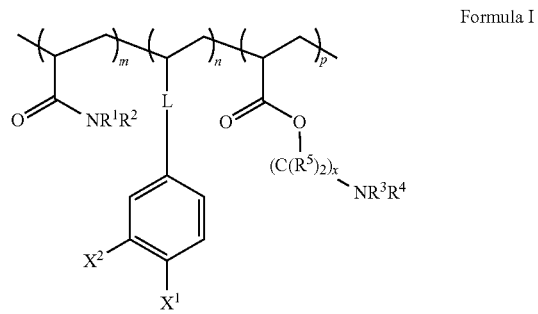

Formula I

The cryogel is formed by mixing the monomers of the co-polymer of Formula I at a temperature of less about 5 degrees C. with the polyol and a free radical initiator in an aqueous solution and polymerizing the solution to form the cryogel. The cryogel is used for culturing cells and can be decomposed by contact with a monosaccharide.

16 Claims, 6 Drawing Sheets

(56) References Cited

OTHER PUBLICATIONS

Lozinsky, V. I., "Cryogels on the basis of natural and synthetic polymers: preparation, properties and areas of implementation," Russ. Chem. Rev. 71, 489-511 (2002).

Lozinsky, V. I., "Polymeric cryogels as promising materials of biotechnological interest," Trends. Biotechnol. 21, 445-451 (2003).

Plieva, F. M., et al., "Cryogel applications in microbiology," Trends. Microbiol. 16(11), 543-551 (2008).

Prud'Homme, R. K., et al., "Polymers in aqueous media: Performance through association," Glass, J.E., Ed., Advances in Chemistry p. 223; American Chemical Society: Washington, DC p. 84, (1989).

Srivastava, A., et al., "The physical characterization of supermacroporous poly(N-isopropylacrylamide) cryogel: Mechanical strength and swelling/de-swelling kinetics," Mater. Sci. Eng. A. 464, 93-100, (2007).

Wise, E. T. et al., "A simple partitioning model for reversibly cross-linked polymers and application to the poly(vinyl alcohol)/borate system ("Slime")," Macromolecules 28, 8321-8327 (1995).

* cited by examiner

CRYOGELS OF PVA-BORONIC ACID CONTAINING CO-POLYMERS FOR CELL CULTURE

CROSS-REFERENCE TO RELATED APPLICATIONS

This application is a U.S. national stage application of International Application No. PCT/IB2011/053522, filed on Aug. 8, 2011, which in turn claims the benefit of India Patent Application 01775/DEL/2011, filed on Jun. 23, 2011, the contents of both of which are incorporated herein by reference in their entirety for any and all purposes.

FIELD

This technology is generally related to polymeric materials and more specifically to polymers for cell culturing and scaffolding.

BACKGROUND

The following description is provided to assist the understanding of the reader. None of the information provided or references cited is admitted to be prior art to the present invention.

Tissue engineering scaffolds are used as supports to accommodate mammalian cell growth and guide the growth in three dimensions. Such scaffolds may be highly porous and provide for three dimensional growth. The pores within such a scaffold may be interconnected with adequate size to allow unhindered cell infiltration and free exchange of nutrients, $O_2$ and waste metabolites between the cells and their environment. The porous structure may also have a variety of pore dimensions, wall thicknesses, and cell diameters to facilitate the growth of cells and formation of tissues. There is need to have a scaffold with the above-mentioned properties.

SUMMARY

In one aspect, the present technology provides a cryogel, which includes a polyol and a phenylboronate containing co-polymer (PCC) of Formula I:

Formula I wherein, m is from 150000 to 220000; n is from 4000 to 6000; p is 0 or from 3500 to 5500; x is from 1 to 5; L is a bond or —CONH— wherein the nitrogen is attached to the substituted phenyl group; $R^1$, $R^2$, $R^3$, and $R^4$ are independently H or $C_1$-$C_6$ alkyl; each $R^5$ independently is H or $C_1$-$C_3$ alkyl; and either $X^1$ is H and $X^2$ is —B(OH)$_2$, or $X^1$ is —B(OH)$_2$ and $X^2$ is H. As used herein, the polymers of the present technology are co-polymers wherein, irrespective of how represented, any constituent monomer may be bonded directly to any constituent monomer. For example, the three monomeric units in the compound represented by Formula I may be in any order, despite what is expressly shown in the representative Formula, or like monomeric units may be in adjacent positions. Random polymers of this sort are well known and understood in the art. In one embodiment, the polymer is: poly-(AAm)$_m$-co-(VPBA)$_n$); poly-((NIPAAm)$_m$-co-(VPBA)$_n$); poly-((AAm)$_m$-co-(AAPBA)$_n$-co-(DMAEMA)$_p$); poly-((NIPAAm)$_m$-co-(AAPBA)$_n$-co-(DMAEMA)$_p$); poly-((NIPAAM)$_m$-co-(VPBA)$_n$-(DMAEMA)$_p$); poly-((AAm)$_m$-co-(VPBA)$_n$-co-(DMAEMA)$_p$); or poly-((DMAAm)$_m$-co-(VPBA)$_n$-co-(DMAEMA)$_p$). As used herein, AAm refers to Acrylamide, AAPBA refers to N-acryloyl-3-aminophenylboronic acid, DMAAm refers to N,N-dimethylacrylamide, DMAEMA refers to N,N-dimethylaminoethylmethacrylate, NIPAAm refers to N-isopropylacrylamide, and VPBA refers to 4-vinylphenylboronic acid. As used herein, -co-, simply indicates that, as already disclosed hereinabove, these polymers are co-polymers, where any monomer can be directly attached to any monomer. Such polymers of the present technology may also be represented without explicitly referring to m, n, and p values, for example, and without limitation, as poly-(AAm-co-AAPBA-co-DMAEMA), where it is understood that in the co-polymer, the monomers are present in numbers as provided in accordance with the present technology. In another embodiment, the polyol is a polyvinyl alcohol or a galactomannan In another embodiment, the present technology provides xerogels of the cryogels of the present technology.

As used herein, the term polyvinyl alcohol (PVA) refers to polymers having an ethylenic alcohol monomeric unit:

As used herein, the term galactomannan(s), refers to refers to natural polysaccharides composed of β(1-4) linked D-mannopyranosyl backbone with random side chains of α(1-6) linked D-galactopyranose. In some embodiments, it is α(1-4)-linked β-D-mannopyranose backbone with branchpoints from their 6-positions linked to α-D-galactose, i.e. a 1-6-linked α-D-galactopyranose.

In another aspect, a method of preparing an aqueous mixture is provided which includes mixing at a temperature of less than about 5° C., a polyol, a radical initiator, a compound of Formula II, a compound of Formula III, and a compound of Formula IV to form the aqueous mixture:

Formula II

Formula III

Formula IV wherein L is a bond or —CONH— wherein the nitrogen is attached to the substituted phenyl group; $R^1$, $R^2$, $R^3$, and $R^4$ are independently H or $C_1$-$C_6$ alkyl; x is from 1 to 5; each $R^5$ independently is H or $C_1$-$C_3$ alkyl; and either $X^1$ is H and $X^2$ is —$B(OH)_2$, or $X^1$ is —$B(OH)_2$ and $X^2$ is H.

In another embodiment, the method further includes polymerizing the compound of Formula II, the compound of Formula III, and the compound of Formula IV to form a cryogel. In another embodiment, the method further includes lyophilizing the cryogel to provide a xerogel. In another embodiment, the cryogel includes the polyol and poly-$(AAm)_m$-co-$(VPBA)_n$; poly-$((NIPAAm)_m$-co-$(VPBA)_n)$; poly-$((AAm)_m$-co-$(AAPBA)_n$-co-$(DMAEMA)_p)$; poly-$((NIPAAm)_m$-co-$(AAPBA)_n$-co-$(DMAEMA)_p)$; poly-$((NIPAAM)_m$-co-$(VPBA)_n$-$(DMAEMA)_p)$; poly-$((AAm)_m$-co-$(VPBA)_n$-$(DMAEMA)_p)$; or poly-$((DMAAm)_m$-co-$(VPBA)_n$-$(DMAEMA)_p)$, wherein m, n, and p is defined as above.

In another aspect, a cell culture medium is provided which includes the cryogel of the present technology. In various embodiments, the cell culture medium is used in a method of cell culture which includes contacting a cell with the culture medium. In some embodiments, the methods include disintegrating the cryogel by contacting the cryogel with a monosaccharide. In some embodiments, the monosaccharide includes glucose, galactose, fructose, sucrose and arabinose.

BRIEF DESCRIPTION OF THE DRAWINGS

FIG. 1A-I are illustrative embodiments of phenylboronate containing co-polymer-polyvinyl alcohol (PCC-PVA) cryogels, where FIGS. 1A and B illustrate poly-(NIPAAm-co-VPBA)-PVA cryogel sheets and monoliths, FIGS. 1C and D depict SEM micrographs of poly-(NIPAAm-co-VPBA)-PVA cryogel, FIGS. 1E and F depict SEM micrographs of poly-(AAm-co-VPBA)-PVA cryogel, FIGS. 1G and H depict SEM micrographs poly-(AAm-co-AAPBA-co-DMAEMA)-PVA cryogel and FIG. 1I depicts a SEM micrograph of poly-(NIPAAm-co-VPBA)-galactomannan cryogel.

DETAILED DESCRIPTION

In the following detailed description, the illustrative embodiments described are not meant to be limiting. Other embodiments may be utilized, and other changes may be made, without departing from the spirit or scope of the subject matter presented here.

As used herein, unless otherwise stated, the singular forms "a," "an," and "the" include plural reference.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Provided herein are cryogels, methods of making them, and methods of using them. As used herein, cryogels are supermacroporous structures with interconnected pores formed through polymerization and/or crosslinking of gel forming precursors in moderately frozen solutions at subzero temperatures. In one aspect, the present technology provides a cryogel, which includes a polyol and a PCC of Formula I:

Formula I where m is from 150000 to 220000; n is from 4000 to 6000; p is 0 or from 3500 to 5500; x is from 1 to 5; L is a bond or —CONH— wherein the nitrogen is attached to the substituted phenyl group; $R^1$, $R^2$, $R^3$, and $R^4$ are independently H or $C_1$-$C_6$ alkyl; each $R^5$ independently is H or $C_1$-$C_3$ alkyl; and either $X^1$ is H and $X^2$ is —$B(OH)_2$, or $X^1$ is —$B(OH)_2$ and $X^2$ is H. In some embodiments, x is 1, or 2, or 3, or 4, or 5.

In one embodiment, m is from 160,000 to 210,000. In another embodiment, m is from 170,000 to 200,000. In another embodiment, m is from 180,000 to 190,000. In another embodiment, n is from 4500 to 5500. In another embodiment, n is about 5000. In another embodiment, p is 0. In another embodiment, p is from 4000 to 5000.

In other embodiments, $R^1$ and $R^2$ are both H, $R^3$ and $R^4$ are both H, or $R^1$, $R^2$, $R^3$, $R^4$ are all H. In yet other embodiments, $R^1$ is H, and $R^2$ is $C_1$-$C_6$ alkyl, or $R^3$ is H, and $R^4$ is $C_1$-$C_6$ alkyl, or $R^1$ and $R^2$ are both $C_1$-$C_6$ alkyl. In another embodiment, $R^3$ and $R^4$ are both $C_1$-$C_6$ alkyl. In another embodiment, at least two of $R^1$, $R^2$, $R^3$, and $R^4$ are $C_1$-$C_6$ alkyl and the rest are H. In another embodiment, $R^1$ and $R^2$ are both H, methyl, ethyl, n-propyl, or iso-propyl. In another embodiment, $R^3$ and $R^4$ are both H, methyl, ethyl, n-propyl, or iso-propyl. In another embodiment, $R^1$ and $R^2$ are both H, methyl, ethyl, n-propyl, or iso-propyl, and $R^3$ and $R^4$ are both methyl, ethyl, n-propyl, or iso-propyl. In another embodiment, $R^1$, $R^2$, $R^3$, and $R^4$ are independently H, unsubstituted $C_1$-$C_6$ alkyl, or $C_1$-$C_6$ alkyl substituted with up to 3 substituents such as hydroxyl, amino, and substituted amino.

In another embodiment, $R^5$ is H. In another embodiment, one of the $R^5$ groups is H and the other $R^5$ group is $C_1$-$C_3$ alkyl.

In another embodiment, L is a bond and $X^1$ is —$B(OH)_2$. In another embodiment, L is —CO—NH— and $X^1$ is H.

The polyol of the cryogel may be a polyvinyl alcohol (PVA), or a galactomannan. Where the polyol is a polyvinyl alcohol, a weight ratio of the PVA to polyphenylboronate containing co-polymer may be from 2:1 to 1:5, from 1:1 to 1:3, or is about 1:2. Where the polyol is a galactomannan, a weight ratio of the PVA to galactomannan may be from 2:1 to 1:5, from 1:1 to 1:3, or is about 1:2.

The PCC may be selected from a wide variety of polyphenylboronate polymers. For example, the PCC may be, but is not limited to, poly((AAm)$_m$-co-(VPBA)$_n$); poly-((NIPAAm)$_m$-co-VPBA)$_n$); poly-((AAm)$_m$-co-(AAPBA)$_n$-co-(DMAEMA)$_p$); poly-((NIPAAm)$_m$-co-(AAPBA)$_n$-co-(DMAEMA)$_p$); poly-((NIPAAM)$_m$-co-(VPBA)$_n$-co-(DMAEMA)$_p$); poly-((AAm)$_m$-co-(VPBA)$_n$-co-(DMAEMA)$_p$); or poly-((DMAAm)$_m$-co-(VPBA)$_n$-co-(DMAEMA)$_p$).

The cryogels above may all be used to culture cells for use in a wide variety of applications, including, but not limited to, cell manufacturing, cell engineering, tissue repair, tissue engineering, or synthetic food or meat. The cryogels may be used with a wide variety of cell culture media and techniques to grow cells. For example, one such medium in which the cryogels may be used is with Dulbecco's modified Eagle's medium (DMEM), and optionally with a serum albumin, and/or an antibiotic. Other media may include serum-free media such as, but not limited to, 293 SFM II, CD 293, FreeStyle 293, Hybridoma-SFM (Invitrogen), and Ex-Cell 293 (JRH Biosciences); dexamethasone (dex); hydrocortisone (HC); and triiodothyronine (T3). Other media with which the cryogels may be used will be recognized by those of skill in the art. Other techniques that may be used include the use of well plates or bioreactors, or the like. The cryogel provide a matrix upon, and/or in, which cells may grow in the various media. The cryogels may be prepared in situ with the various media, or they may be separately prepared and introduced to the media, or they may be prepared, sterilized and then introduced to the media. Illustrative media include, but are not limited to, Eagle's Modified Essential Medium (EMEM), Roswell Park Memorial Institute Medium (RPMI Medium), RPMI 1640, Glasgow's Minimal Essential Medium (GMEM), Ham's F-12 Medium, Iscove's Modified Dulbecco's Medium (IMDM), McCoy's-5A, CMRL-1066, and MCDB-104, 105, 110, 151, 201, 302, 411, and the like. Culturing techniques employed with conventional tissue engineering scaffolds may also be used with cryogels.

Xerogels may also be prepared from the cryogels. As used herein, xerogels are a lyophilized cryogel, and which have substantially no moisture. Xerogels may be prepared by the heating and dehydration of cryogels, or through freeze-drying of the cryogel. As used herein, xerogels are cryogels, and which have substantially no moisture. As used herein, substantially no moisture means that the xerogel contains less than 10 wt % water. Thus, in some embodiments, the cryogel contains less than 9 wt %, or less than 8 wt % water, less than 7 wt %, or less than 6 wt % water, less than 5 wt %, or less than 4 wt % water, less than 3 wt %, or less than 2 wt % water, less than 1 wt %, or less than 0.5 wt % water, less than 0.1 wt %, or less than 0.05 wt % water, In some embodiments, a xerogel has from about 0.001 wt % to about 1 wt % water.

In another aspect, a method is provided for preparing an aqueous mixture of a cryogel. The method includes mixing at a temperature of less than about 5° C., a polyol, a radical initiator, and either compounds of Formula II and III, or compounds of Formula II, III, and IV, to form the aqueous mixture:

Formula II

Formula III

Formula IV

In the above formulas, L is a bond or —CONH— wherein the nitrogen is attached to the substituted phenyl group; $R^1$, $R^2$, $R^3$, and $R^4$ are independently H or $C_1$-$C_6$ alkyl; x is from 1 to 5; each $R^5$ independently is H or $C_1$-$C_3$ alkyl; and either $X^1$ is H and $X^2$ is —$B(OH)_2$, or $X^1$ is —$B(OH)_2$ and $X^2$ is H. In other embodiments, $R^1$, $R^2$, $R^3$, $R^4$, L, $X^1$, $X^2$, x and x are defined above.

In the aqueous mixtures, the cryogel is present from about 1 wt % to about 20 wt %. In some embodiments, the cryogel is present in the water from about 1 wt % to about 10 wt %. In the aqueous mixtures of the cryogels, the ratios of the compounds range as follows: polyol:radical initiator:Formula II:Formula III:Formula IV are, respectively, about 2-8:5-10:0.5-2:0-0.5 by weight. In another embodiment, the ratio is about 5:9:1:0.3:0 by weight, respectively (i.e. the compound of Formula IV is absent).

As the mixture is being formed, or shortly after it is formed, the compounds polymerize to form the cryogel as prompted by the radical initiator. Once formed, in some embodiments, the cryogel is then lyophilized to provide the corresponding xerogel. The cryogel may include the polyol and a co-polymer of Formula I which may be, but is not limited to, poly-(AAm-co-VPBA); poly-(NIPAAm-co-VPBA); poly-((AAm)$_m$-(AAPBA)$_n$-(DMAEMA)$_p$); poly-((NIPAAm)$_m$-(AAPBA)$_n$-(DMAEMA)$_p$); poly-((NIPAAM)$_m$-(VPBA)$_n$-(DMAEMA)$_p$); poly-((AAm)$_m$-(VPBA)$_n$-(DMAEMA)$_p$); or poly-((DMAAm)$_m$-(VPBA)$_n$-(DMAEMA)$_p$), where values of m, n, and p include those disclosed above for the co-polymer of Formula I. In some embodiments, the polyol is PVA or a galactomannan.

In some embodiments, the polymerization is performed for about 20 hours, about 15 hours, or about 10 hours. In another embodiment, the polymerization is carried out at about −20° C., about −10° C., or at about −5° C.

A variety of radical initiators, polymerization accelerators and polymerization promoters may be used to prepare the cryogels. In one embodiment, the radical initiator includes a persulfate, an azo compound, an azoisoalkylnitrile, or $Fe^{2+}$. In another embodiment, the polymerization accelerator or the polymerization promoter includes N,N,N',N'-tetramethylethylenediamine, alkylamine, or cobalt naphthalene.

In another aspect, a method of cell culture is provided including contacting a cell with a culture medium including a cryogel. The culture medium may include a material such as, but not limited to, Dulbecco's modified Eagle's medium, a serum albumin, or an antibiotic.

In another aspect, a method of disintegrating any of the above cryogels is provided. The method may include contacting the cryogel with a monosaccharide, thereby disintegrating the cryogel. In some embodiments, the monosaccharide includes glucose, galactose, fructose, sucrose and arabinose. The concentration of the monosaccharide that may be employed to disintegrate the cryogels is from about 0.1M-0.5M.

As used herein, "alkyl" groups are monovalent hydrocarbon radicals and include straight chain and branched alkyl groups having from 1 to about 20 carbon atoms, and typically from 1 to 12 carbons or, in some embodiments, from 1 to 8 carbon atoms. As also used herein, "alkyl groups" include cycloalkyl groups as defined below. Examples of straight chain alkyl groups include without limitation methyl, ethyl, n-propyl, n-butyl, n-pentyl, n-hexyl, n-heptyl, and n-octyl groups. Examples of branched alkyl groups include, without limitation, isopropyl, sec-butyl, t-butyl, neopentyl, and isopentyl groups. Alkyl groups may be unsubstituted or substituted. Representative substituted alkyl groups may be substituted one or more times with, for example, amino, carboxyl, thio, hydroxy, cyano, alkoxy, phenyl, and/or F, Cl, Br, and I groups.

As used herein, "alkoxy" refers to an —O-alkyl moiety. Examples of alkoxy groups include, without limitation, methoxy, ethoxy, isopropoxy, and benzyloxy.

As used herein, "cycloalkyl" groups are monovalent cyclic hydrocarbons. Examples of cyloalkyl groups include, without limitation, cyclopropyl, cyclobutyl, cyclopentyl, and cyclohexyl. Cycloalkyl groups may be unsubstituted or substituted.

As used herein, "substituted amino" refers to —NHR$^x$ or —N(R$^x$)$_2$ wherein each R$^x$ independently is alkyl, —CO-alkyl, CO$_2$-alkyl, SO$_2$-alkyl, or two R$^x$ groups together with the nitrogen atom to which they are bonded for a cyclic ring.

The present technology, thus generally described, will be understood more readily by reference to the following example, which is provided by way of illustration and is not intended to limit the present technology.

EXAMPLES

Example 1

Method of Preparing of PCC-polyol Based Cryogels

Figure 1:
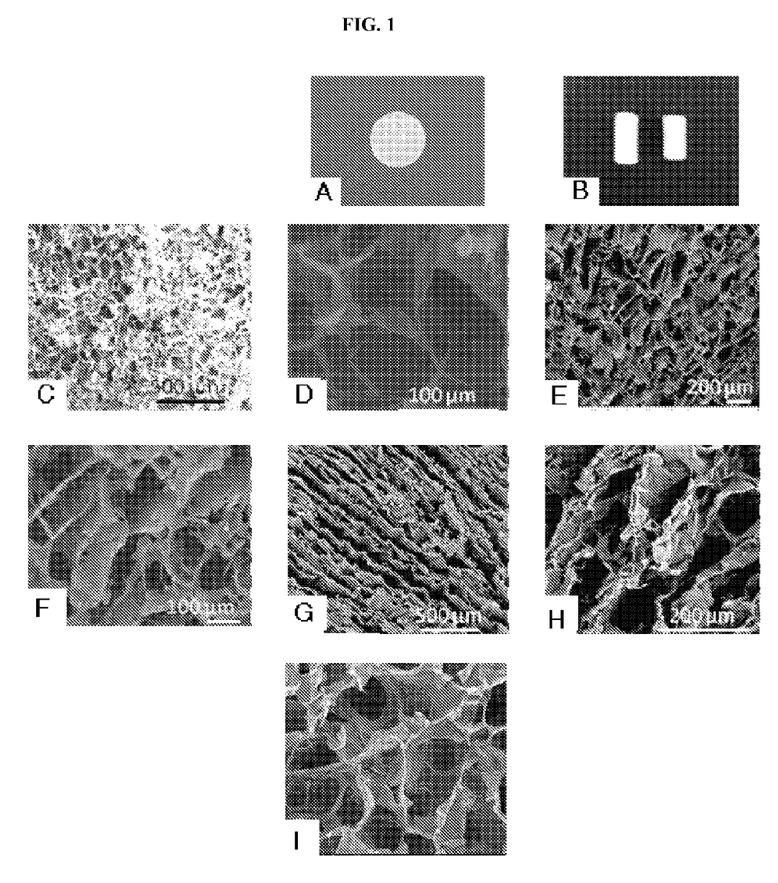
Figure 2:
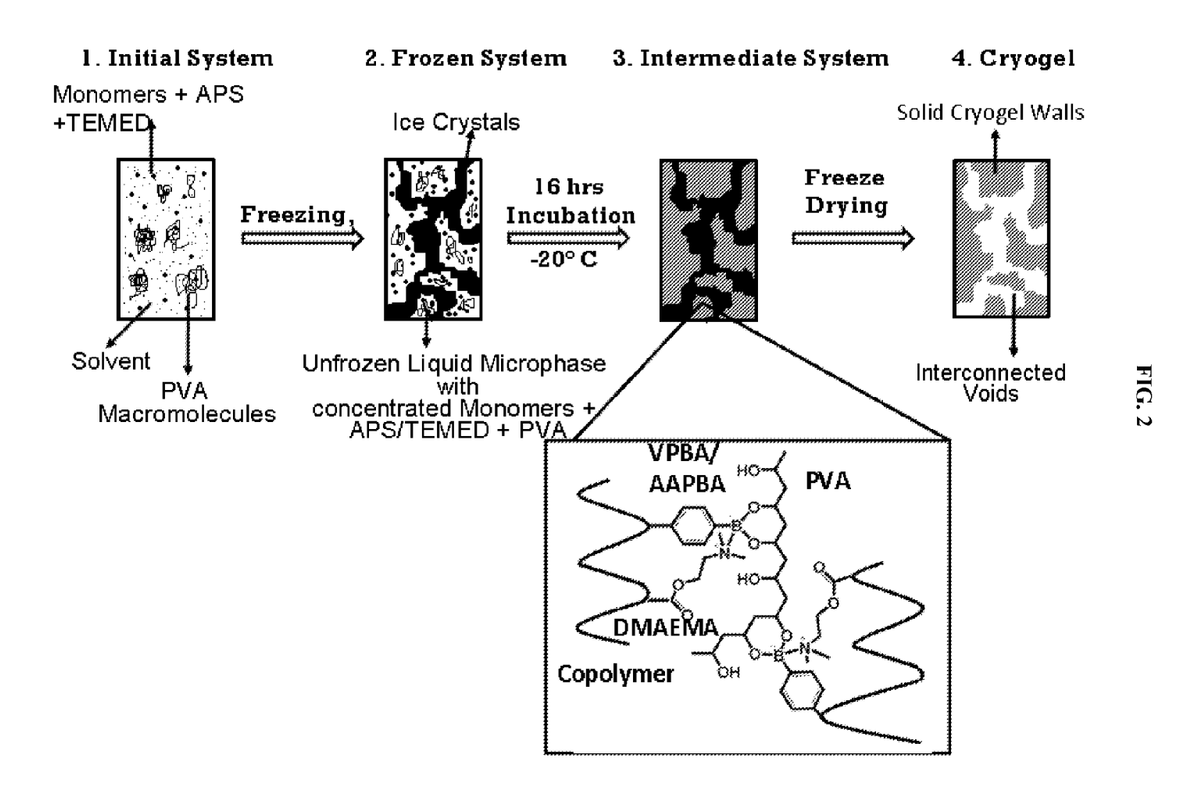
FIG. 2 depicts an illustrative embodiment of synthesizing PCC-PVA cryogels.

Cryogel sheets and monoliths including poly-(NIPAAm-co-VPBA), poly-(AAm-co-VPBA) and poly-(AAm-co-AAPBA-co-DMAEMA) and PVA or galactomannan (see photos in FIG. 1a-I) were synthesized by cryogenic co-polymerization of the precursor monomers in the presence of PVA at −20° C. for 18 hours without any bi-functional crosslinking agents like bis-acrylamide. Following freezing, the gel precursor system includes Unfrozen Liquid Microphase (UFLMP) and the frozen solvent crystals. Due to cryo-concentration, UFLMP includes high concentrations of monomers and PVA. Ammonium persulfate (APS) and N,N,N',N'-tetramethylethylenediamine (TEMED) initiate the co-polymerization of monomers along with VPBA. Without being bound by mechanism, on attaining sufficient length, the co-polymer chains are cross-linked by PVA via intermolecular multipoint monodiols resulting in solid cryogel walls. As used herein, monodiol refers to the complex formed between a boronate/borate moiety and adjacent hydroxyl groups (1,2- or 1,3-cis diols) of a diol/polyol through the release of two water molecules. The frozen solvent crystals are continuous throughout the system resulting in an open porous system upon freeze drying (FIG. 2).

Example 1A

Poly-(NIPAAm-co-VPBA)-PVA Cryogel

NIPAAm (900 mg), VPBA (100 mg), and TEMED (39 μl) were completely dissolved in de-gassed 100 mM NaOH solution (10 mL, pH~13) (a total monomer concentration of 10%) and nitrogen bubbled for 20 min. PVA (500 mg) was dissolved in degassed 100 mM NaOH (9.5 mL) by heating at 90° C. under magnetic stirring for 30-45 min, cooled to room temperature and then APS (30 mg) dissolved in degassed water (0.5 mL) was added to it. The monomer-TEMED and PVA-APS solutions were pre-cooled to 4° C. The solutions are mixed and immediately transferred to a 2.5 mL disposable syringe kept in the cryostat (Lauda, Proline PR 1840, Germany) maintained −20° C. The final 20 mL solution includes 5% monomer and 2.5% PVA. Cryogelation was carried out for 18 h. After 18 h the poly-(NIPAAm-co-VPBA)-PVA cryogels were slowly thawed (0.11° C./min) and freeze-dried.

Example 1B

Poly-(AAm-co-VPBA)-PVA Cryogels

Poly-(AAm-co-VPBA)-PVA cryogels were prepared in essentially the same manner as described above except that AAm (900 mg) was used instead of NIPAAm.

Example 1C

Poly(NIPAAm-co-VPBA)-galactomannan Cryogels

Poly-(NIPAAm-co-VPBA)-galactomannan cryogels were prepared essentially in the same manner as mentioned above except that Guar Gum (900 mg, SD Fine, India) dissolved in degassed 100 mM NaOH (9.5 mL) was used in the place of PVA. Guar gum is a plant gum composed of galactomannans, a natural polysaccharide composed of a linear backbone of β(1-4) linked D-mannopyranose with random side chains of α(1-6) linked D-galactopyranose with mannose and galactose in 2:1 ratio.

Example 1D

Poly-(AAm-co-AAPBA-co-DMAEMA)-PVA Cryogels

N-Acryloyl-3-aminophenylboronic Acid (AAPBA) was synthesized as reported in Ivanov et al. Polymer 45; 2495-

2505 (2004). AAPBA (100 mg) was dissolved in double distilled (DD) de-gassed water (10 mL, pH ~7.4) at 60° C. for 15-20 min followed by cooling to room temperature. AAm (800 mg), DMAEMA (107 μL) and TEMED (19.5 μL) were completely dissolved in the AAPBA solution (a total monomer concentration of 10%) and nitrogen bubbled for 20 min PVA (500 mg) was then dissolved in DD degassed water (9.5 mL, pH ~7.4) by heating at 90° C. under magnetic stirring for 30-45 min, cooled to room temperature and then APS (15 mg) dissolved in 0.5 mL of degassed water was added to it. The monomer-TEMED and PVA-APS solutions were then cooled to 4° C. The solutions were mixed and immediately transferred to 2.5 mL disposable syringes kept in the cryostat maintained at −20° C. The final 20 mL solution includes 5 wt % monomer and 2.5 wt % PVA. Cryogelation was carried out for 18 h. After 18 h poly-(AAm-co-AAPBA-co-DMAEMA) cryogels were slowly thawed (0.11° C./min) and freeze-dried.

Example 2

Fructose Induced Cryogel Disintegration

For testing monosaccharide induced disintegration of the cryogels, poly-(NIPAAm-co-VPBA)-PVA, poly-(AAm-co-VPBA)-PVA and poly-(AAm-co-AAPBA-co-DMAEMA)-PVA cryogels, and fructose at 100 mM, 500 mM and 1 M, were employed. Phosphate buffer (10 mM) without any monosaccharide was used as control.

Cryogel samples of predetermined dry weight (i.e. xerogels; approximately 110 mg-147 mg) were transferred into 50 mL centrifuge tubes each containing 10 mL of fructose-phosphate buffer solutions. The tubes were incubated at 37° C. and centrifuged at 60-90 rpm. The fructose-phosphate buffer solution was changed once every 5 days. All the studies were carried out in duplicate and after 15 days the cryogel samples were taken out and freeze-dried for 48 h before being weighed. The percentage reduction in dry weight of each cryogel sample in response to the specific fructose concentration was plotted against time. The percentage reduction in cryogel dry weights after 15 days of fructose treatment is presented in Table 1.

cryogel. NIPAAm polymer chains are known for their thermo-responsive behavior with a lower critical solution temperature (LCST) of approximately 32° C. Accordingly, the temperature used in the disintegration studies, i.e., 37° C., presents a hydrophobic environment for the poly-(NIPAAm-co-VPBA) chains in the cryogel. As a result, the co-polymer chains may find it difficult to dissociate from the PVA chains in response to fructose. This may explain the slower disintegration of poly-(NIPAAm-co-VPBA)-PVA cryogels in response to poly-(AAm-co-VPBA)-PVA cryogels.

The objective of this experiment is to show the ability of monosaccharide solutions, fructose by way of example, to disintegrate PCC-Polyol cryogels. All three cryogels are treated with fructose solutions of three different concentrations for 15 days. In order to demonstrate that the cryogels get disintegrated only in the presence of a monosaccharide such as fructose in the solution, a control is established where all the three cryogels were also treated with a plain buffer solution without any fructose in it, for 15 days. As used herein, the control refers to all the three PCC-polyol cryogels treated with fructose-free solution whereas the remaining subjects refer to all the three cryogels treated with the fructose solutions. All the three cryogels showed significant disintegration when treated with fructose solutions compared to treatment with plain buffer (control). However poly-(NIPAAm-co-VPBA)-PVA cryogel showed relatively slower disintegration compared to other two PCC-Polyol cryogels.

Example 3

Compression Testing Analysis of PCC-PVA Cryogels

Compression tests were performed on the three cryogels in order to obtain their stress-strain data and elastic moduli. Cylindrical cryogel samples of poly-(NIPAAm-co-VPBA)-PVA (height: 11 mm; cross-section 50.265 mm$^2$), poly-(AAm-co-VPBA)-PVA (height: 10.3 mm; cross-section 51.53 mm$^2$) and poly-(AAm-co-AAPBA-co-DMAEMA)-PVA (height: 17 mm; cross-section 56.745 mm$^2$) were used for the tests. The cylindrical samples were subjected to

TABLE 1

Fructose Induced Disintegration of synthesized PCC-PVA Cryogels after 15 days.

| No. | Cryogel | Percentage Reduction in Cryogel Dry Weight After 15 Days in Response to | | | |
| --- | --- | --- | --- | --- | --- |
| | | Control | 100 mM Fructose | 500 mM Fructose | 1 M Fructose |
| 1 | Poly-(NIPAAm-co-VPBA)-PVA | 12.453 ± 0.667 | 28.41 ± 2.195 | 61.225 ± 2.195 | 79.484 ± 1.939 |
| 2 | Poly-(AAm-co-VPBA)-PVA | 19.365 ± 0.805 | 51.835 ± 3.335 | 78.165 ± 1.635 | 100 |
| 3 | Poly-(AAm-co-AAPBA-co-DMAEMA)-PVA | 19.07 ± 0.676 | 100 | 100 | 100 |

Figure 3:
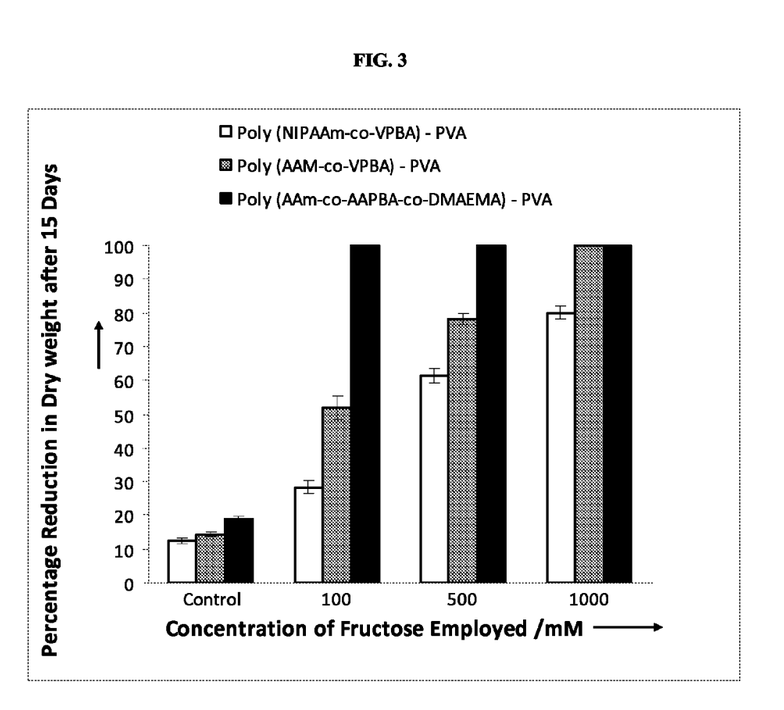
FIG. 3 is a graph of percent reduction in dry weights of different PCC-PVA cryogels in response to fructose treatment over 15 days.

After 15 days, the fructose treated PCC-PVA cryogels showed significant gel-sol transition in response to fructose when compared to controls (FIG. 3). Poly-(AAm-co-AAPBA-co-DMAEMA)-PVA cryogels, in particular, showed 100% disintegration within 15 days in response to fructose concentrations as low as 100 mM. The relatively low percentage reduction in dry weight exhibited by poly-(NIPAAm-co-VPBA)-PVA cryogels when compared to poly-(AAm-co-VPBA)-PVA cryogels is probably due to the presence of the NIPAAm in the co-polymer chains of former uniaxial stress using an Instron 1195 computerized testing machine with 100 KN load cell under displacement control at the rate of 1 mm/min. The elastic modulus of the samples was determined from the elastic deformation portion of stress-strain graph using the formula: Elastic Modulus (Pa)= ($\Delta$Load/Cross Section)/($\Delta$l/Original Sample Height), where $\Delta$l refers to the change in length of the sample with respect to a change in the load by $\Delta$Load.

Figure 4A:
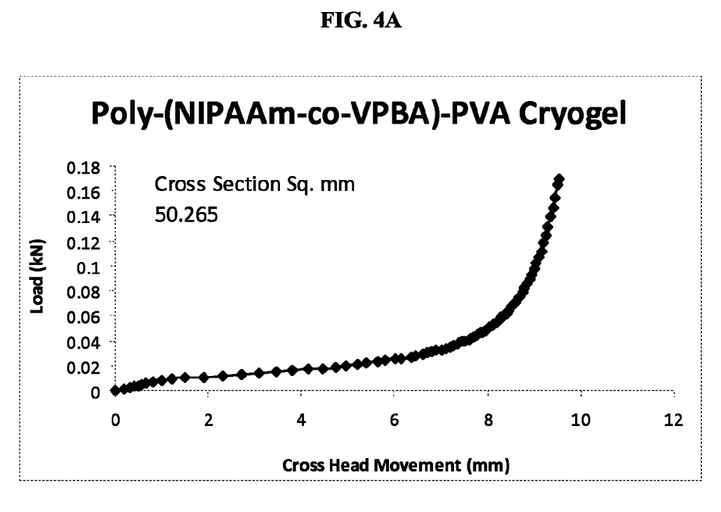
FIGS. 4A, B, and C are illustrative embodiments of stress-strain properties of the cryogels, with FIG. 4A depicting that of poly-(NIPAAm-co-VPBA)-PVA, FIG. 3B depicting that of poly-(AAm-co-VPBA)-PVA, and FIG. 4C depicting that of poly-(AAm-co-AAPBA-co-DMAEMA)-PVA cryogels, under uniaxial compression with 100 kN load cell under displacement control at the rate of 1 mm/min.
Figure 4B:
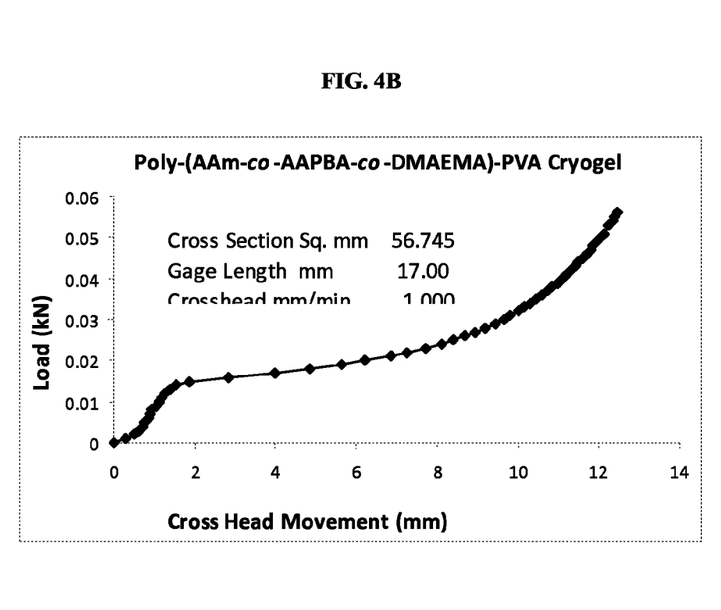
Figure 4C:
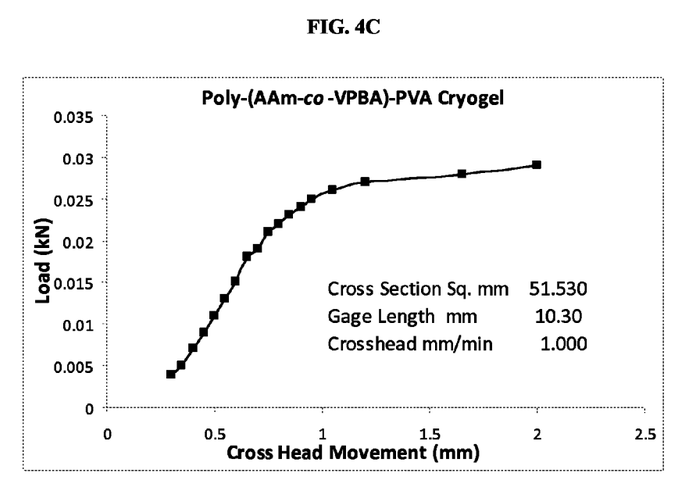

Elastic moduli of the cryogels were calculated from the elastic deformation portions of respective load Vs deformation plots (FIGS. 4A, 4B, and 4C). Elastic modulus, in general, represents the stiffness of a material. The relatively high elastic moduli of PCC-PVA cryogels when compared to traditional pure poly-(NIPAAm) and poly-(AAm) cryogels (with elastic moduli usually in the range of KPa) may arise from the presence of PVA. Poly-(AAm-co-VPBA)-PVA cryogel has highest elastic modulus of about 7.195 MPa followed by poly-(AAm-co-AAPBA-co-DMAEMA)-PVA (3.895 MPa) and poly-(NIPAAm-co-VPBA)-PVA (2.172 MPa) cryogels. The results of compression tests of PCC-PVA cryogels demonstrated their usefulness in tissue engineering applications. The cryogels possess adequate mechanical and/or viscoelastic properties to withstand the forces generated by growing tissue as well as those generated while handling in the clinical phase without any deformation. The elastic moduli of PCC-PVA based cryogels are in the range of 2-7 MPa, indicating superior mechanical properties and ability to support tissue growth without any deformation or mechanical failure.

Example 4

In Vitro Cell Viability and Proliferation Studies

FDA/DAPI Double Staining Cylindrical cryogel sections of poly-(NIPAAm-co-VPBA)-PVA, poly-(AAm-co-VPBA)-PVA and poly-(AAm-co-AAPBA-co-DMAEMA)-PVA of 8 mm diameter and 1 mm thickness were washed with excess amounts of deionized water to remove unreacted monomers, and in the case of VPBA containing cryogels, traces of alkalinity. The cryogel sections were sterilized by placing each section in 2 mL of 2% penicillin-streptomycin solution for 48 h. Then the sections were transferred to a 24-well non-treated polystyrene plate (Nunc, Roskilde, Denmark), with one section in each well. NIH3T3 fibroblasts ($5.5 \times 10^4$ cells) suspended in DMEM (100 µl) were directly seeded on to the scaffolds followed by the addition of DMEM (1 mL) supplemented with 10% FBS and 1% penicillin-streptomycin solution. The cell seeded scaffolds were incubated at 37° C. in an incubator with humidified 5% $CO_2$ environment. The medium was refreshed every 2 days and the cell proliferation was monitored regularly under an inverted microscope (Nikon YS100, Japan). After 12 days of cell culture, the medium was removed and the scaffolds are washed with cold PBS (1.5 mL). The cell scaffolds were then stained with fluorescein diacetate (FDA, 500 µL, 5 µg/mL, working concentration), a vital dye, for 5 min and 200 µl of 4',6-diamidino-2-phenylindole (DAPI) (0.1 µg/mL, working concentration) for 15 min DAPI stains both viable and non-viable cells. After 15 min, the dyes were pipetted out and the scaffolds were washed twice gently with 1.5 mL of cold phosphate buffer saline (PBS) in order to remove excess dye. The cell distribution and viability in FDA/DAPI stained cryogel sections were immediately observed under fluorescence microscope (Zeiss, Axioscope 2 plus, Germany). The images of DAPI stained cells (both viable and non viable) were taken with a DAPI filter, those of FDA stained viable cells were taken with a FITC (Fluorescein isothiocyanate) filter.

At the same magnification and specimen position, the images of the scaffold were taken under a bright field light. All the three individual images were then merged into a RGB image using Adobe Photoshop. Fluorescein diacetate (FDA), a non-fluorescent and non-polar compound, readily enters the cell by penetrating cell membranes and gets hydrolyzed by intracellular esterases into polar fluorescein which passes slowing through living cell membrane, accumulates inside the cell and fluoresces green when irradiated with blue light [excitation: 495 nm; emission: 520 nm]. As a result, viable cells fluoresce, brilliant green under blue light. 4',6-diamidino-2-phenylindole (DAPI) is a fluorescent dye that binds strongly to the minor groove of DNA and fluoresces under UV light [excitation: 358 nm; emission: 471 nm]. Since it can pass through intact cell membranes it stains both viable and non viable cells in a given specimen. Therefore in a merged image of FDA and DAPI stained cells, greenish cyan portions indicate viable cells whereas isolated blue portions indicate non viable cells.

RGB images of poly-(AAm-co-VPBA)-PVA cryogel section with cells at day 12 merged from the individual bright field image of scaffold, FDA images of viable cells and DAPI image of all cells were obtained. The images indicated good cell viability even at day 12. Merged RGB images of poly-(AAm-co-AAPBA-co-DMAEMA)-PVA and poly-(NIPAAm-co-VPBA)-PVA cryogels also showed good amounts of cell viability with negligible or no dead cells. Therefore FDA/DAPI double staining of PCC-PVA cryogels showed their competency to support cell growth and viability.

To test the viability and proliferation of cells cultured on PCC-PVA cryogels, 3-(4,5-dimethylthiazol-2-yl)-2,5-diphenyltetrazolium bromide (MTT) assay was carried out on poly-(AAm-co-AAPBA-co-DMAEMA)-PVA cryogel sections. MTT assay is an indirect method for assessing cell activity and proliferation. Mitochondrial enzymes of viable cells may oxidize yellow MTT into purple formazan which can be dissolved in a suitable solvent and quantified by a spectrophotometer.

Thin cryogel sections (8 mm diameter, 3 mm thickness) were sterilized with a 2% antibiotic solution for 48 h and were directly seeded with NIH3T3 fibroblasts ($1.5 \times 10^5$) suspended in DMEM (200 µL). DMEM (1 mL), supplemented with 10% FBS and 1% penicillin-streptomycin solution, was added in to each scaffold containing well. NIH3T3 fibroblasts ($1.5 \times 10^5$) seeded on to 12-well tissue culture polystyrene (TCPS) plates (Axygen Life Sciences, Union City, USA) were used as control. Both the cell loaded cryogels and controls were incubated at 37° C. in an incubator with humidified 5% $CO_2$ atmosphere. At each interval, the culture medium was removed from the test wells and gently washed with cold PBS (100 mM). The serum-free DMEM medium (0.5 mL) containing MTT at a working concentration of 0.5 mg/mL, was added to the wells and incubated at 37° C. for 5 h. The MTT reagent in each well was gently replaced with dimethylsulfoxide (DMSO, 1.5 mL), which dissolves intracellular purple formazan crystals to give blue-violet colored solution. The absorbance of this solution was then determined at 570 nm. The viability and proliferation of cells cultured on PCC-PVA cryogels, 3-(4,5-dimethylthiazol-2-yl)-2,5-diphenyltetrazolium bromide (MTT) assay was carried out on NIH3T3 seeded AADP cryogel sections on alternate days for 10 days.

Figure 5:
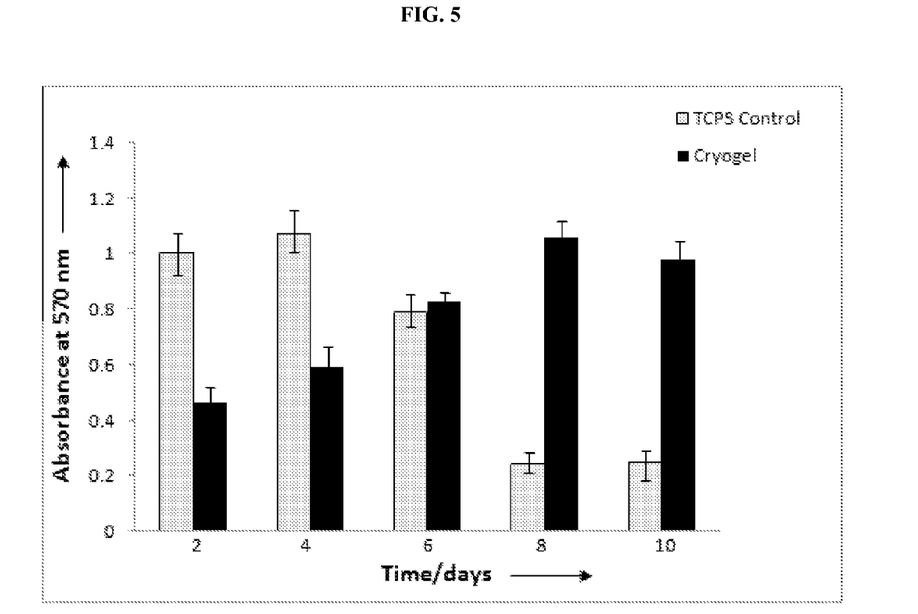
FIG. 5 is a graph showing the relative viability of fibroblast (NIH3T3) cells in poly-(AAm-co-AAPBA-co-DMAEMA)-PVA (AADP) cryogels as determined by MTT assay, where light colored columns represent viability in the TCPS control and dark colored columns represent viability in the cryogel.

The results obtained for the cryogels were compared with those of control TCPS dishes seeded with same number of cells (FIG. 5). During the first few days (up to day 4) cell metabolic activity was low in case of cryogels when compared to 2D-controls. Later, the cryogels demonstrated appreciable cellular activity, whereas controls showed a decline. Without being bound by mechanism, the high surface area available in the cryogel scaffolds for cells to live and proliferate when compared to control 2D-scaffolds may result in the improved utility of the PCC-PVA cryogel as a cell culture medium.

EQUIVALENTS

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms 'comprising,' 'including,' 'containing,' etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase 'consisting essentially of' will be understood to include those elements specifically is recited and those additional elements that do not materially affect the basic and novel characteristics of the claimed technology. The phrase 'consisting of' excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compounds, compositions, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, or compounds, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' 'at least,' 'greater than,' 'less than,' and the like, include the number recited and refer to ranges which can be subsequently broken down into subranges as discussed above. Finally, as will be understood by one skilled in the art, a range includes each individual member.

Other embodiments are set forth in the following claims.

The invention claimed is:

1. A cryogel comprising a polyol and a co-polymer of Formula I:

Formula I wherein,
m is from 150000 to 220000;
n is from 4000 to 6000;
p is 0 or from 3500 to 5500;
x is from 1 to 5;
L is a bond or —CONH— wherein the nitrogen is attached to the boron-substituted phenyl group;
$R^1$, $R^2$, $R^3$, and $R^4$ are independently H or $C_1$-$C_6$ alkyl;
each $R^5$ independently is H or $C_1$-$C_3$ alkyl; and
either $X^1$ is H and $X^2$ is —B(OH)$_2$, or X is —B(OH)$_2$ and $X^2$ is H;
wherein the polyol is polyvinyl alcohol or galactomannan.

2. The cryogel of claim 1, wherein $R^1$, $R^2$, $R^3$, and $R^4$ are H.

3. The cryogel of claim 1, wherein at least two of $R^1$, $R^2$, $R^3$, and $R^4$ are $C_1$-$C_6$ alkyl.

4. The cryogel of claim 1, wherein $R^1$, $R^2$, $R^3$, and $R^4$ are $C_1$-$C_6$ alkyl.

5. The cryogel of claim 1, wherein L is a bond and $X^1$ is —B(OH)$_2$ or $X^2$ is —B(OH)$_2$.

6. The cryogel of claim 1, wherein L is —CO—NH— and $X^1$ is H or $X^2$ is H.

7. The cryogel of claim 1, wherein $R^5$ is H.

8. The cryogel of claim 1, wherein x is 1 or 2.

9. The cryogel of claim 1, wherein the co-polymer is:
poly-((AAm)$_m$-co-(VPBA)$_n$);
poly-((NIPAAm)$_m$-co-VPBA)$_n$);
poly-((AAm)$_m$-co-(AAPBA)$_n$-co-(DMAEMA)$_p$);
poly-((NIPAAm)$_m$-co-(AAPBA)$_n$-co-(DMAEMA)$_p$);
poly-((NIPAAM)$_m$-co-(VPBA)$_n$-co-(DMAEMA)$_p$);
poly-((AAm)$_m$-co-(VPBA)$_n$-co-(DMAEMA)$_p$); or
poly-((DMAAm)$_m$-co-(VPBA)$_n$-co-(DMAEMA)$_p$).

10. A cell culture medium comprising the cryogel of claim 1.

11. The cryogel of claim 1 that is a xerogel.

12. A method of preparing an aqueous mixture comprising:
mixing at a temperature of less than about 5° C., a polyol, a radical initiator, a compound of Formula II, a compound of Formula III, and optionally a compound of Formula IV to form the aqueous mixture:

Formula II

Formula III

Formula IV wherein

L is a bond or —CONH— wherein the nitrogen is attached to the boron-substituted phenyl group;

$R^1$, $R^2$, $R^3$, and $R^4$ are independently H or $C_1$-$C_6$ alkyl;

x is from 1 to 5;

each $R^5$ independently is H or $C_1$-$C_3$ alkyl; and either $X^1$ is H and $X^2$ is —B(OH)$_2$, or $X^1$ is —B(OH)$_2$ and $X^2$ is H;

wherein the polyol is polyvinyl alcohol or galactomannan.

13. The method of claim 12, further comprising polymerizing the compounds of the aqueous mixture to form a cryogel.

14. The method of claim 12, wherein the cryogel comprises the polyol and a co-polymer which is:

poly-((AAm)$_m$-co-((VPBA)$_n$);
poly-((NIPAAm)$_m$-co-(VPBA)$_n$);
poly-((AAm)$_m$-co-(AAPBA)$_n$-co-(DMAEMA)$_p$),
poly-((NIPAAm)$_m$-co-(AAPBA)$_n$-co-(DMAEMA)$_p$);
poly-((NIPAAM)$_m$-co-(VPBA)$_n$-co-(DMAEMA)$_p$);
poly-((AAm)$_m$-co-(VPBA)$_n$-co-(DMAEMA)$_p$); or
poly-((DMAAm)$_m$-co-(VPBA)$_n$-co-(DMAEMA)$_p$);

wherein m is from 150000 to 220000;

n is from 4000 to 6000; and p is 0 or is from 3500 to 5500.

15. A method of cell culture comprising contacting a cell with a culture medium comprising the cryogel of claim 1, thereby culturing the cell.

16. A method of disintegrating the cryogel of claim 1, comprising contacting the cryogel with a monosaccharide, thereby disintegrating the cryogel.

* * * * *

UNITED STATES PATENT AND TRADEMARK OFFICE
CERTIFICATE OF CORRECTION

Page 1 of 1

PATENT NO.        : 8,569,062 B2
APPLICATION NO.   : 13/880020
DATED             : October 29, 2013
INVENTOR(S)       : Kumar It is certified that error appears in the above-identified patent and that said Letters Patent is hereby corrected as shown below:

In the Specifications

In Column 2, Line 35, delete "galactomannan" and insert -- galactomannan. --, therefor.

In Column 13, Line 23, delete "is recited" and insert -- recited --, therefor.

In the Claims

In Column 16, Line 12, in Claim 14, delete "(DMAEMA)$_p$)," and insert -- (DMAEMA)$_p$); --, therefor.

Signed and Sealed this
First Day of April, 2014

Michelle K. Lee
*Deputy Director of the United States Patent and Trademark Office*